US007241802B2

(12) United States Patent
Hinze et al.

(10) Patent No.: US 7,241,802 B2
(45) Date of Patent: Jul. 10, 2007

(54) SUBSTITUTED CYCLOHEXYLCARBOXYLIC ACID AMIDE COMPOUNDS

(75) Inventors: Claudia Hinze, Aachen (DE); Bernd Sundermann, Aachen (DE); Hans Schick, Berlin (DE)

(73) Assignee: Gruenenthal GmbH, Aachen (DE)

( * ) Notice: Subject to any disclaimer, the term of this patent is extended or adjusted under 35 U.S.C. 154(b) by 0 days.

(21) Appl. No.: 11/594,935

(22) Filed: Nov. 9, 2006

(65) Prior Publication Data
US 2007/0105941 A1 May 10, 2007

Related U.S. Application Data

(63) Continuation of application No. PCT/EP2005/004908, filed on May 6, 2005.

(30) Foreign Application Priority Data

May 10, 2004 (DE) .................. 10 2004 023 632

(51) Int. Cl.
*C07D 209/20* (2006.01)
*C07C 233/58* (2006.01)
*A61K 31/404* (2006.01)
*A61K 31/16* (2006.01)

(52) U.S. Cl. .............. 514/419; 514/613; 548/495; 564/191

(58) Field of Classification Search .......... 548/495; 564/191; 514/419, 613
See application file for complete search history.

(56) References Cited

U.S. PATENT DOCUMENTS

| 7,173,045 B2* | 2/2007 | Sundermann et al. ........ 514/330 |
| 2004/0063935 A1* | 4/2004 | Yasuda et al. ................ 544/60 |
| 2004/0162287 A1* | 8/2004 | Sundermann et al. .... 514/231.2 |
| 2004/0229926 A1* | 11/2004 | Yasuda et al. ............... 514/365 |
| 2005/0277674 A1* | 12/2005 | Hinze et al. ................. 514/323 |

FOREIGN PATENT DOCUMENTS

| EP | 1 325 910 A1 | 7/2003 |
| WO | WO 98/25897 | 6/1998 |
| WO | WO 01/87838 A1 | 11/2001 |
| WO | WO 02/090317 A1 | 11/2002 |

OTHER PUBLICATIONS

International Search Report dated Sep. 5, 2005 with English translation (four (4) pages).
German Search Report dated Nov. 11, 2004 with English translation of relevant portion (seven (7) pages).
Toshiya Manabe et al., "Facilitation of Long-Term Potentiation and Memory in Mice Lacking Nociceptin Receptors", Letters To Nature, Aug. 6, 1998, pp. 577-581, vol. 394, Macmillan Publishers Ltd.
Miyuki Nishi et al., "Unrestrained Nociceptive Response and Disregulation of Hearing Ability in Mice Lacking the Nociceptin/OrphaninFQ Receptor," The EMBO Journal, 1997, pp. 1858-1864, vol. 16, No. 8, Oxford University Press.
Girolamo Calo et al., "Pharmacology of Nociceptin and its Receptor: A Novel Therapeutic Target," British Journal of Pharmacology, 2000, pp. 1261-1283, 129, Macmilian Publishers Ltd.
Daniel Lednicer et al., "4-Amino-4-arylcyclohexanones and Their Derivatives, a Novel Class of Analgesics", J. Med. Chem., 1980, pp. 424-430, 23.
Ali Ardati et al., "Interaction of [$^3$H]Orphanin FQ and $^{125}$I-Tyr14-Orphanin FQ with the Orphanin FQ Receptor Kinetics and Modulation by Cations and Guanine Nucleotides," Molecular Pharmacology, 1997, pp. 816-824, 51, The American Society for Pharmacology and Experimental Therapeutics.
E.G. Gray, et al. "The Isolation of Nerve Endings from Brain: An Electron-Microscopic Study of Cell Fragments Derived By Homogenization and Centrifugation", Journal of Anatomy, 1962, pp. 79-88, vol. 96, Part 1.
Martin Ch. Frink et al., "Influence of Tramadol of Neurotransmitter Systems of the Rat Brain", Arzneim-Forsch Drug Res., 1996, pp. 1029-1036, vol. 46 (II), Nr. 11.

* cited by examiner

*Primary Examiner*—Fiona T Powers
(74) *Attorney, Agent, or Firm*—Crowell & Moring LLP

(57) ABSTRACT

Substituted cyclohexylcarboxylic acid amide compounds, processes for their production, pharmaceutical compositions containing these compounds and the use of substituted cyclohexylcarboxylic acid compounds for producing pharmaceutical compositions for treating conditions or disease states associated with the opioid receptor system and/or with noradrenalin and/or serotonin re-uptake.

21 Claims, No Drawings

SUBSTITUTED CYCLOHEXYLCARBOXYLIC ACID AMIDE COMPOUNDS

CROSS REFERENCE TO RELATED APPLICATIONS

This application is a continuation of international application no. PCT/EP2005/004908, filed May 6, 2005 designating the United States of America and published in German on Nov. 24, 2005 as WO 2005/110977, the entire disclosure of which is incorporated herein by reference. Priority is claimed based on Federal Republic of Germany patent application no. DE 10 2004 023 632.1, filed May 10, 2004.

BACKGROUND OF THE INVENTION

The present invention relates to substituted cyclohexylcarboxylic acid amide compounds, to processes for their production, to pharmaceutical compositions containing these compounds and to the use of cyclohexylcarboxylic acid compounds for producing pharmaceutical compositions.

The treatment of chronic and non-chronic pain conditions has great importance in medicine. There is a worldwide need for effective methods of treating pain. The urgent need for action for patient-oriented and purposeful treatment of chronic and non-chronic pain conditions, this being taken to mean the successful and satisfactory treatment of pain for the patient, is documented in the large number of scientific papers which have recently appeared in the field of applied analgesics and fundamental research work on nociception.

Conventional μ-opioids such as morphine are very effective in the treatment of strong to very strong pain and are of great importance for the treatment of pain. However, it may be advantageous if, in addition to the μ-opioid receptor, other opioid receptors, in particular the ORL1 receptor, are affected since the pure μ-opioids also exhibit undesired side effects such as obstipation and respiratory depression, but may also lead to dependency. The opioid receptors δ, κ and ORL1 are also involved in the occurrence of pain (Opioids: Introduction, pp. 127-150, Further Opioid Receptors, 455-476 in: Analgesics—From Chemistry and Pharmacology to Clinical Application, Wiley VCH, 2002).

It is also known that influencing of serotonin and/or noradrenalin re-uptake can be beneficial to the effects and side effects of opioids (Example: Tramadol, cf. Opioids with Clinical Relevance: Tramadol, 228-230 in: Analgesics—From Chemistry and Pharmacology to Clinical Application, Wiley VCH, 2002).

The ORL1 receptor is also involved in the regulation of further physiological and pathophysiological processes. These include inter alia learning and memory formation (Manabe et al., Nature, 394, 1997, pp. 577-581), Hörvermögen [Hearing capacity] (Nishi et al., EMBO J., 16, 1997, pp. 1858-1864) and numerous further processes. In a synopsis by Calo et al. (Br. J. Pharmacol. 129, 2000-1261) there is an overview of the indications or biological procedures, in which the ORL1 receptor plays a part or could highly probably play a part. Mentioned inter alia are: analgesia, stimulation and regulation of nutrient absorption, effect on μ-agonists such as morphine, treatment of withdrawal symptoms, reduction of the addiction potential of opioids, anxiolysis, modulation of motor activity, memory disturbances, epilepsy; modulation of neurotransmitter release, in particular of glutamate, serotonin and dopamine, and therefore neurodegenerative diseases; affecting the cardiovascular system, triggering an erection, diuresis, anti-natriuresis, electrolyte balance, arterial blood pressure, water-retention diseases, intestinal motility (diarrhoea), relaxation of the respiratory tract, micturition reflex (urinary incontinence). The use of agonists and antagonists as anoretics, analgesics (also when administered with opioids) or nootropics will also be discussed.

Structurally related compounds are known from the prior art (WO 02090317) which have an affinity with the ORL1 receptor. An effect on noradrenalin and serotonin re-uptake has not previously been described for this structural class.

SUMMARY OF THE INVENTION

It is an object of the present invention to provide new pharmaceutically active compounds which act on the opioid receptor system.

Another object of the invention is to provide pharmaceutical compositions for treatment or inhibition of various conditions or disease states associated with the opioid receptor system.

A further object of the invention is to provide a process for producing such compounds.

An additional object of the invention is to provide a method of treating or inhibiting various conditions or disease states known to be associated with the opioid receptor system.

It is also an object of the invention to provide compounds which influence noradrenalin and serotonin re-uptake.

The invention therefore relates to substituted cyclohexylcarboxylic acid amide derivatives of general formula I,

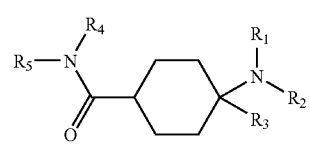

wherein

R$^1$ and R$^2$ independently of one another represent H; CHO; respectively saturated or unsaturated, branched or unbranched, singly or multiply substituted or unsubstituted C$_{1-5}$ alkyl; respectively saturated or unsaturated, singly or multiply substituted or unsubstituted C$_{3-8}$ cycloalkyl; or respectively singly or multiply substituted or unsubstituted aryl, C$_{3-8}$ cycloalkyl or heteroaryl bound by C$_{1-3}$ alkyl; or R$^1$ and R$^2$ together represent CH$_2$CH$_2$O CH$_2$CH$_2$, CH$_2$CH$_2$NR$^{10}$CH$_2$CH$_2$ or (CH$_2$)$_{3-6}$, wherein R$^{10}$ represents H; respectively saturated or unsaturated, branched or unbranched, singly or multiply substituted or unsubstituted C$_{1-5}$ alkyl; respectively saturated or unsaturated, singly or multiply substituted or unsubstituted C$_{3-8}$ cycloalkyl; respectively singly or multiply substituted aryl or heteroaryl; or respectively singly or multiply substituted or unsubstituted aryl, C$_{3-8}$ cycloalkyl or heteroaryl bound by C$_{1-3}$ alkyl;

R$^3$ represents respectively saturated or unsaturated, branched or unbranched, singly or multiply substituted or unsubstituted C$_{1-5}$ alkyl; respectively saturated or unsaturated, singly or multiply substituted or unsubstituted C$_{3-8}$ cycloalkyl; respectively unsubstituted or singly or multiply substituted aryl, heteroaryl or C$_{3-8}$ cycloalkyl bound by a C$_{1-3}$ alkyl group; respectively unsubstituted or singly or multiply substituted naphthyl, anthracenyl, thiophenyl, benzothiophenyl, furyl, benzofuranyl, benzodioxolanyl, indolyl, indanyl, benzodioxanyl, pyrrolyl, pyridyl, pyrimidyl or pyrazinyl; phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert.-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl;

$R^4$ represents $-(CR^6R^7)_nR^8$, wherein n represents 0, 1, 2, 3, 4, 5 or 6

$R^6$ represents H or saturated or unsaturated, branched or unbranched, unsubstituted or singly or multiply substituted $C_{1-5}$ alkyl, $R^7$ represents H, saturated or unsaturated, branched or unbranched, unsubstituted or singly or multiply substituted $C_{1-5}$ alkyl, or COOR$^9$, wherein R$^9$ represents H or saturated or unsaturated, branched or unbranched, unsubstituted or singly or multiply substituted $C_{1-5}$ alkyl; or $R^6$ and $R^7$ form a ring $(CH_2)_kCHR^8(CH_2)_m$, where k=1, 2 or 3 and m=1 or 2; and $R^8$ represents respectively unsubstituted or singly or multiply substituted cycloalkyl, aryl or heteroaryl;

$R^5$ represents H or $-(CH_2)_lR^8$, wherein l represents 1, 2 or 3, or $R^4$ and $R^5$ together represent $CH_2CH_2OCH_2CH_2$ or $CH_2CH_2NR^{11}CH_2CH_2$, wherein $R^{11}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

in the form of the racemate; the enantiomers, diastereomers, mixtures of the enantiomers or diastereomers or an individual enantiomer or diastereomer; the bases and/or salts of physiologically acceptable acids or cations.

The compounds according to the invention exhibit good binding to the μ-receptor and to the ORL1 receptor but also to other opioid receptors. Surprisingly it has been found that the compounds are also good inhibitors of noradrenalin and serotonin re-uptake. They are therefore also capable of treating depression and/or bulimia and/or anorexia and/or catalepsy and/or anxiolysis and/or increasing alertness and/or libido. The terms "$C_{1-5}$ alkyl" and "$C_{1-3}$ alkyl", according to this invention, include acyclic saturated or unsaturated hydrocarbon radicals, which may be branched or straight chained and unsubstituted or singly or multiply substituted, with 1, 2, 3, 4 or 5 C atoms or 1, 2 or 3 C atoms, i.e. $C_{1-5}$ alkanyls, $C_{2-5}$ alkenyls and $C_{2-5}$ alkynyls or $C_{1-3}$ alkanyls, $C_{2-3}$ alkenyls and $C_{2-3}$ alkynyls. Alkenyls have at least one C=C double bond and alkynyls at least one C≡C treble bond. Alkyl is advantageously selected from the group comprising methyl, ethyl, n-propyl, 2-propyl, n-butyl, iso-butyl, sec.-butyl, tert.-butyl, n-pentyl, iso-pentyl, neo-pentyl, n-hexyl, 2-hexyl; ethylenyl (vinyl), ethynyl, propenyl ($-CH_2CH=CH_2$, $-CH=CH-CH_3$, $-C(=CH_2)-CH_3$), propynyl ($-CH-C\equiv CH$, $-C\equiv C-CH_3$), 1,1-dimethylethyl, 1,1-dimethylpropyl, butenyl, butinyl, pentenyl and pentynyl.

For the purposes of this invention the term "cycloalkyl" or "$C_{3-8}$ cycloalkyl" denotes cyclic hydrocarbons with 3, 4, 5, 6, 7 or 8 carbon atoms, wherein the hydrocarbons may be saturated or unsaturated (but not aromatic), unsubstituted or singly or multiply substituted. With respect to cycloalkyl, the term also comprises saturated or unsaturated (but not aromatic) cycloalkyls, in which one or two carbon atoms are replaced by a heteroatom, S, N or O. $C_{3-8}$ cycloalkyl is advantageously selected from the group comprising cyclopropyl, cyclobutyl, cyclopentyl, cyclohexyl, cycloheptyl, cyclooctyl, cyclopentenyl, cyclohexenyl, cycloheptenyl and cyclooctenyl, but also tetrahydropyranyl, dioxanyl, dioxolanyl, morpholinyl, piperidinyl, piperazinyl, pyrazolinonyl and pyrrolidinyl.

The term "$(CH_2)_{3-6}$" denotes $-CH_2-CH_2-CH_2-$, $-CH_2-CH_2-CH_2-CH_2-$, $-CH_2-CH_2-CH_2-CH_2-CH_2-$ and $CH_2-CH_2-CH_2-CH_2-CH_2-CH_2$.

The term "aryl", according to this invention, denotes carbocyclic ring systems comprising at least one aromatic ring, but without heteroatoms in only one of the rings, inter alia phenyls, naphthyls and phenanthrenyls, fluoranthenyls, fluorenyls, indanyls and tetralinyls. The aryl radicals can also be condensed with further saturated, (partially) unsaturated or aromatic ring systems. Each aryl radical can be unsubstituted or singly or multiply substituted, the aryl substituents being the same or different and in any desired or possible position of the aryl. Phenyl or naphthyl radicals are particularly advantageous.

The term "heteroaryl" represents a 5-, 6- or 7-membered cyclic aromatic radical, which contains at least 1, optionally also 1, 2, 3, 4 or 5 heteroatoms, wherein the heteroatoms may be the same or different and the heterocycle may be unsubstituted or singly or multiply substituted; in the case of substitution on the heterocycle, the substituents may be the same or different and in any desired or possible position of the heteroaryl. The heterocycle may also be part of a bi- or polycyclic system. Preferred heteroatoms are nitrogen, oxygen and sulphur. It is preferred for the heteroaryl radical to be selected from the group comprising pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxazolyl, isoxazolyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein the binding with the compounds of general structure I can be made via any desired and possible ring member of the heteroaryl radical.

In conjunction with "alkyl", the term "substituted", according to this invention, denotes substitution of one or more hydrogen radicals by F, Cl, Br, I, —CN, =O, $NH_2$, NH-alkyl, NH-aryl, NH-heteroaryl, NH-cycloalkyl, NH-alkyl-aryl, NH-alkyl-heteroaryl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-aryl, S-heteroaryl, S-alkyl-aryl, S-alkyl-heteroaryl, S-cycloalkyl, S-alkyl-OH, S-alkyl-SH, OH, O-alkyl, O-aryl, O-heteroaryl, O-alkyl-aryl, O-alkyl-heteroaryl, O-cycloalkyl, O-alkyl-OH, CHO, $C(=O)C_{1-6}$-alkyl, $C(=S)C_{1-6}$-alkyl, $C(=O)$aryl, $C(=S)$aryl, $C(=O)C_{1-6}$-alkyl-aryl, $C(=S)C_{1-6}$-alkyl-aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $C(=O)NH_2$, $C(=O)$NH-alkyl, $C(=O)$NH-aryl, $C(=O)$NH-cycloalkyl, $C(=O)N(alkyl)_2$, $C(=O)N(alkyl-aryl)_2$, $C(=O)N(alkyl-heteroaryl)_2$, $C(=O)N(cycloalkyl)_2$, SO-alkyl, $SO_2$-alkyl, $SO_2NH_2$, $SO_3H$, $PO(O-C_{1-6}-alkyl)_2$, $Si(C_{1-6}-alkyl)_3$, $Si(C_{3-8}-cycloalkyl)_3$, $Si(CH_2-C_{3-8}-cycloalkyl)_3$, $Si(phenyl)_3$,-cycloalkyl, aryl or heteroaryl, wherein multiply substituted radicals are taken to mean those which are either multiply, for example doubly or trebly, substituted on different atoms or the same atoms, for example trebly on the same carbon atom, as in the case of $CF_3$ or —$CH_2CF_3$ or at different positions, as in the case of —CH(OH)—CH=$CHCHCl_2$. Multiple substitution can take place with the same substituent or with different substituents. A substituent may optionally also be substituted for its part; thus —O-alkyl also includes inter alia —O—$CH_2$—$CH_2$—O—$CH_2$—$CH_2$—OH.

With respect to "aryl", "heteroaryl" and "cycloalkyl", according to this invention, "singly or multiply substituted" denotes the single or multiple, for example double, treble, quadruple or quintuple, substitution of one or more hydrogen atoms of the ring system by F, Cl, Br, I, CN, $NH_2$, NH-alkyl, NH-aryl, NH-heteroaryl, NH-alkyl-aryl, NH-alkyl-heteroaryl, NH-cycloalkyl, NH-alkyl-OH, $N(alkyl)_2$, $N(alkyl-aryl)_2$, $N(alkyl-heteroaryl)_2$, $N(cycloalkyl)_2$, $N(alkyl-OH)_2$, $NO_2$, SH, S-alkyl, S-cycloalkyl, S-aryl, S-heteroaryl, S-alkyl-aryl, S-alkyl-heteroaryl, S-cycloalkyl, S-alkyl-OH, S-alkyl-SH, OH, O-alkyl, O-cycloalkyl, O-aryl, O-heteroaryl, O-alkyl-aryl, O-alkyl-heteroaryl, O-cycloalkyl, O-alkyl-OH, CHO, $C(=O)C_{1-6}$-alkyl, $C(=S)C_{1-6}$-alkyl, $C(=O)$aryl, $C(=S)$aryl, $C(=O)$-$C_{1-6}$-alkyl-aryl, $C(=S)C_{1-6}$-alkyl-aryl, $C(=O)$-heteroaryl, $C(=S)$-heteroaryl, $C(=O)$-cycloalkyl, $C(=S)$-cycloalkyl, $CO_2H$, $CO_2$-alkyl, $CO_2$-alkyl-aryl, $C(=O)NH_2$, $C(=O)$NH-alkyl, $C(=O)$NH-aryl, $C(=O)$NH-cycloalkyl, $C(=O)N(alkyl)_2$, $C(=O)N(alkyl-aryl)_2$, $C(=O)N(alkyl-heteroaryl)_2$, $C(=O)N(cycloalkyl)_2$, S(O)-alkyl, S(O)-aryl, $SO_2$-alkyl, $SO_2$-aryl, $SO_2NH_2$, $SO_3H$, $CF_3$, =O, =S; alkyl, cycloalkyl, aryl and/or heteroaryl; on one atom or optionally on different atoms (wherein a substituent can, in turn, optionally be substituted). Multiple substitution takes place here using the same or different substituents.

The term "salt" denotes any form of the active ingredient according to the invention in which it assumes or is charged with an ionic form and is coupled to a counter ion (a cation or anion) or is in solution. This also includes complexes of the active ingredient with other molecules and ions, in particular complexes complexed by ionic interactions. In particular this denotes (and this is also a preferred embodiment of this invention) physiologically acceptable salts, in particular physiologically acceptable salts with cations or bases and physiologically acceptable salts with anions or acids or even a salt formed with a physiologically acceptable acid or physiologically acceptable cation.

The term "physiologically acceptable salt with anions or acids", according to this invention denotes salts of at least one of the compounds according to the invention—usually protonated, for example on nitrogen—as a cation with at least one anion which are physiologically acceptable—in particular when applied to humans and/or mammals. According to this invention this denotes, in particular, the salt formed with a physiologically acceptable acid, namely salts of the respective active ingredient with inorganic or organic acids which are physiologically acceptable—in particular when applied to humans and/or mammals. Examples of physiologically acceptable salts of certain acids include salts of: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, phosphoric acid, maleic acid, malonic acid, hippuric acid and/or aspartic acid. The hydrochloride salt, the citrate and the hemicitrate are particularly preferred.

The term "salt formed with a physiologically acceptable acid", according to this invention, denotes salts of the respective active ingredient with inorganic or organic acids which are physiologically acceptable—in particular when applied to humans and/or mammals. The hydrochloride and the citrate are particularly preferred. Examples of physiologically acceptable acids include: hydrochloric acid, hydrobromic acid, sulphuric acid, methane sulphonic acid, formic acid, acetic acid, oxalic acid, succinic acid, malic acid, tartaric acid, mandelic acid, fumaric acid, lactic acid, citric acid, glutamic acid, saccharic acid, monomethyl sebacic acid, 5-oxo-proline, hexane-1-sulphonic acid, nicotinic acid, 2-, 3- or 4-amino benzoic acid, 2,4,6-trimethyl-benzoic acid, α-lipoic acid, acetyl glycine, O-acetylsalicylic acid, hippuric acid and/or aspartic acid.

The term "physiologically acceptable salt with cations or bases", according to this invention, denotes salts of at least one of the compounds according to the invention—usually a (deprotonated) acid—as an anion with at least one, preferably inorganic, cation, which are physiologically acceptable, in particular when applied to humans and/or mammals. The salts of the alkali and alkaline-earth metals are particularly preferred, but also ammonium salts, in particular however (mono) or (di) sodium, (mono) or (di) potassium, magnesium or calcium salts.

The term "salt formed with a physiologically acceptable cation", according to this invention denotes salts of at least one of the respective compounds as an anion with at least one inorganic cation, which are physiologically acceptable, in particular when applied to humans and/or mammals. The salts of the alkali and alkaline-earth metals are particularly preferred, but also ammonium salts, in particular however (mono) or (di) sodium, (mono) or (di) potassium, magnesium or calcium salts.

In a preferred embodiment of the substituted cyclohexylcarboxylic acid derivatives according to the invention $R^1$ and $R^2$ independently of one another represent H; saturated or unsaturated, branched or unbranched, singly or multiply substituted or unsubstituted $C_{1-5}$ alkyl; or $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ represents H; saturated or unsaturated, branched or unbranched, singly or multiply substituted or unsubstituted $C_{1-5}$ alkyl. Particularly preferred are substituted cyclohexylcarboxylic acid derivatives, wherein $R^1$ and $R^2$ independently of one another represent $CH_3$ or H, but $R^1$ and $R^2$ do not simultaneously represent H.

Also preferred are substituted cyclohexylcarboxylic acid derivatives, wherein $R^3$ represents respectively unsubstituted or singly or multiply substituted cyclopentyl, cyclohexyl, naphthyl, thiophenyl, benzothiophenyl, furyl, benzofuranyl, benzodioxolanyl, indolyl, indanyl, benzodioxanyl or pyridyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group; phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert.-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl.

Particularly preferred are compounds in which $R^3$ represents respectively unsubstituted or singly or multiply substituted naphthyl, thiophenyl or pyridyl; respectively unsubstituted or singly or multiply substituted $C_{5-6}$ cycloalkyl, phenyl, naphthyl, thiophenyl or pyridyl bound by a saturated, unbranched $C_{1-2}$ alkyl group; phenyl, 2-fluorophenyl, 3-fluorophenyl, 4-fluorophenyl, 2-chlorophenyl, 4-chlorophenyl, 3-chlorophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert.-butylphenyl, 4-fluoro-3-chlorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl or 4-chloro-3-trifluoromethyl.

Especially particularly preferred are substituted cyclohexylcarboxylic acid derivatives, wherein $R^3$ represents substituted or unsubstituted pyridyl, or phenyl, 2-fluorophenyl, 3-fluorophenyl or 4-fluorophenyl, in particular phenyl.

Also preferred are substituted cyclohexylcarboxylic acid derivatives, wherein $R^6$ represents H and $R^7$ represents H or $COOR^9$.

Also preferred are substituted cyclohexylcarboxylic acid derivatives, wherein $R^5$ represents H.

Also preferred are substituted cyclohexylcarboxylic acid derivatives, wherein $R^8$ represents respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzo[1,2,5]thiazolyl or 1,2-dihydroacenaphtenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl.

Particularly preferred are compounds in which $R^8$ represents respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

Especially particularly preferred are substituted cyclohexylcarboxylic acid derivatives, wherein $R^8$ represents respectively singly or multiply substituted phenyl or indolyl.

Most preferred are substituted cyclohexylcarboxylic acid derivatives selected from the group consisting of:
2-[(4-dimethylamino-4-phenyl-cyclohexanecarbonyl)-amino]-3-(1H-indol-3-yl)-propionic acid methylester-hydrochloride; non-polar diastereomer;
2-[(4-dimethylamino-4-phenyl-cyclohexanecarbonyl)-amino]-3-(1H-indol-3-yl)-propionic acid methylester-hydrochloride; polar diastereomer;
4-dimethylamino-4-phenyl-cyclohexanecarboxylic acid (3-phenyl-propyl)amide hydrochloride; non-polar diastereomer; and
4-dimethylamino-4-phenyl-cyclohexanecarboxylic acid (3-phenyl-propyl)amide hydrochloride; polar diastereomer, in the form of the racemate; the enantiomers, diastereomers, mixtures of the enantiomers or diastereomers or an individual enantiomer or diastereomer; the bases and/or salts of physiologically acceptable acids or cations.

The substances according to the invention act, for example, on the ORL1 receptor that is relevant in connection with various diseases, so they are suitable as a pharmaceutical active ingredient in a pharmaceutical composition. The invention therefore also relates to pharmaceutical compositions containing at least one substituted cyclohexylcarboxylic acid derivative according to the invention, and optionally suitable additives and/or auxiliaries and/or optionally further active ingredients.

The pharmaceutical compositions according to the invention optionally contain, in addition to at least one substituted cyclohexylcarboxylic acid derivative according to the invention, suitable additives and/or auxiliary agents, therefore also excipients, fillers, solvents, diluents, dyes and/or binders and can be administered as liquid pharmaceutical compositions in the form of injection solutions, drops or juices, as semi-solid pharmaceutical compositions in the form of granules, tablets, pellets, patches, capsules, plasters or aerosols. The choice of auxiliary agents, etc. and the quantities thereof to be used depend on whether the pharmaceutical composition is to be applied orally, perorally, parenterally, intravenously, intraperitoneally, intradermally, intramuscularly, intranasally, buccally, rectally or topically, for example to the skin, the mucous membranes or the eyes. Preparations in the form of tablets, dragees, capsules, granules, drops, juices and syrups are suitable for oral application, solutions, suspensions, easily reconstitutable dry preparations and sprays are suitable for parenteral, topical and inhalative applications. Substituted cyclohexylcarboxylic acid derivatives according to the invention in a deposit, in dissolved form or in a plaster, optionally with the addition of agents to promote skin penetration, are suitable percutaneous application preparations. Orally or percutaneously applicable preparation forms can release the substituted cyclohexylcarboxylic acid derivatives according to the invention after a delay. The substituted cyclohexylcarboxylic acid derivatives according to the invention can also be applied in the form of parenteral long-acting repositories such as implants or implanted pumps. In principle, further active ingredients known to the person skilled in the art can be added to the pharmaceutical compositions according to the invention.

The quantity of active ingredient to be administered to the patient varies as a function of the weight of the patient, the method of application, the indication and the severity of the illness. Conventionally, 0.00005 to 50 mg/kg, preferably 0.01 to 5 mg/kg of at least one substituted cyclohexylcarboxylic acid derivative according to the invention are applied.

For all of the above-mentioned forms of the pharmaceutical compositions according to the invention, it is particularly preferred if, in addition to at least one substituted cyclohexylcarboxylic acid derivative, the pharmaceutical composition contains a further active ingredient, in particular an opioid, preferably a strong opioid, in particular morphine, or an anaesthetic, preferably hexobarbital or halothane.

In a preferred form of the pharmaceutical composition, a contained substituted cyclohexylcarboxylic acid derivative is in the form of a pure diastereomer and/or enantiomer, as a racemate or as a non-equimolar or equimolar blend of the diastereomers and/or enantiomers.

Both the ORL1 receptor and the further opioid receptors have been identified in particular in the occurrence of pain. Accordingly, substituted cyclohexylcarboxylic acid derivatives according to the invention can be used for producing a pharmaceutical composition for the treatment of pain, in particular acute, neuropathic or chronic pain.

The invention therefore also relates to the use of a substituted cyclohexylcarboxylic acid derivative according to the invention for producing a pharmaceutical composition for treating pain, in particular acute, visceral, neuropathic or chronic pain.

The invention also relates to the use of a substituted cyclohexylcarboxylic acid derivative according to the invention for the treatment of anxiety, stress and stress-related syndromes, depression, catalepsy, epilepsy, Alzheimer's disease, senile dementia, general cognitive dysfunction, learning and memory difficulties (as a nootropic), withdrawal symptoms, alcohol- and/or drug- and/or medicines abuse and/or dependency, sexual dysfunction, cardiovascular diseases, hypotension, hypertension, tinnitus, pruritus, migraine, hearing difficulties, deficient intestinal motility, impaired nutrient absorption, anorexia, obesity, locomotive disorders, diarrhoea, cachexia, urinary incontinence or as a muscle relaxant, anti-convulsive or anaesthetic for co-administration in treatment with an opioid analgesic or anaesthetic, for diuresis or anti-natriuresis, anxiolysis, for modulation of motor activity, for modulation of neurotransmitter release and treatment of neurodegenerative diseases associated therewith, for the treatment of withdrawal symptoms and/or for reducing the potential for addiction to opioids.

In one of the above uses it may be preferred if a substituted cyclohexylcarboxylic acid derivative used is present as a pure diastereomer and/or enantiomer, as a racemate or as non-equimolar or equimolar mixture of diastereomers and/ or enantiomers.

The invention also relates to a process for the treatment, in particular in one of the above-mentioned indications, of a non-human mammal or a human, which or who requires treatment of pain, in particular chronic pain, by administration of a therapeutically effective dose of a substituted cyclohexylcarboxylic acid derivative according to the invention, or of a pharmaceutical composition according to the invention.

The invention also relates to a process for producing the substituted cyclohexylcarboxylic acid derivatives according to the invention as stated in the following description and examples.

General Synthesis Pattern

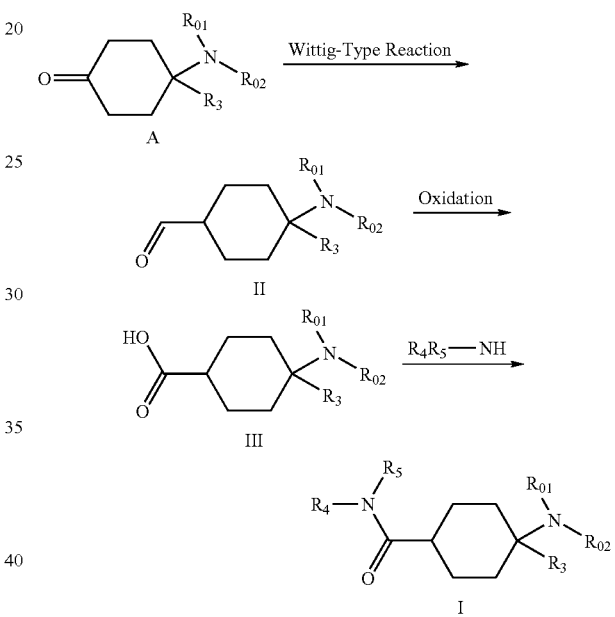

$R^{01}$ and $R^{02}$ have the meaning of $R^1$ and $R^2$ and can additionally assume the meaning of a protecting group.

The production of suitable 4-aminocyclohexanones according to formula A is known from the literature (Lednicer et al., J. Med. Chem. 23, 1980, 424-430; WO 0290317).

An alkoxymethyl-phosphonium salt, preferably methoxymethyl-triphenyl phosphonium chloride or methoxymethyltriphenylphosphonium bromide, is firstly reacted with a strong base, preferably potassium-tert.butylate, sodium hydride or butyllithium, and then with a 4-aminocyclohexanone according to formula A. A cyclohexylcarbaldehyde according to formula II is produced.

The cyclohexylcarbaldehyde II is oxidized with a suitable oxidizing agent, preferably with potassium permanganate, chromium(VI)oxide or other chromium(VI)-salts, to form corresponding cyclohexylcarboxylic acid according to formula III.

The carboxylic acid according to formula III as such or as its corresponding hydrochloride is reacted with a dehydrating reagent, preferably with a carbodiimide, more preferably with dicyclohexyl-carbodiimide, in the presence of an activation reagent, preferably with 1-hydroxybenzotriazole, with an amine of formula $R^4R^5NH$ to form the corresponding amide according to formula I.

The protecting groups at $R^{O1}$ and $R^{O2}$ are optionally subsequently cleaved by methods known to a person skilled in the art.

Alternative Method of Synthesis:

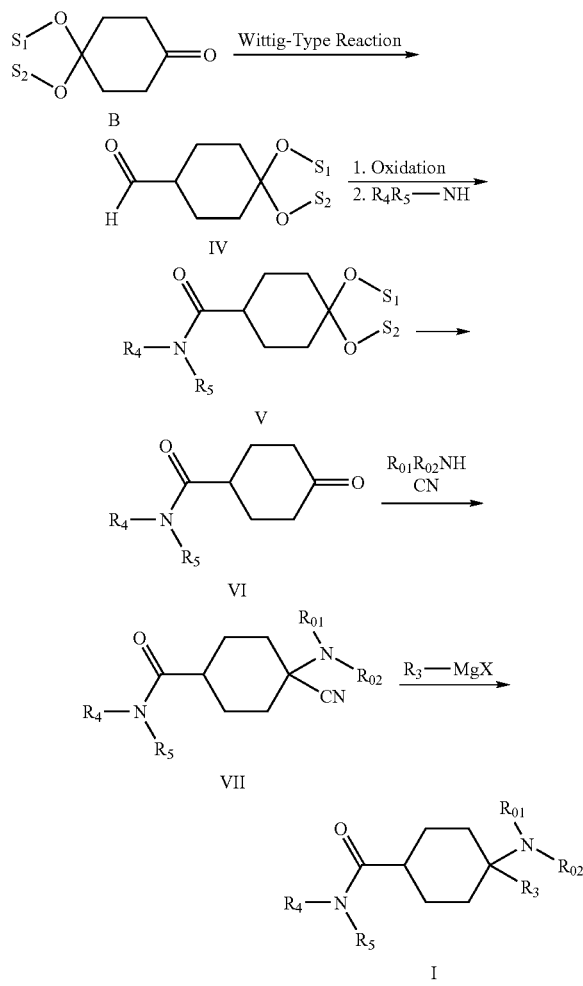

A cyclohexane-1,4-dione according to formula B, protected by the groups $S^1$ and $S^2$, which represent protecting groups—for example substituted or unsubstituted alkyl, in particular $(CH_2)_n$ where n=2-4, is reacted in the presence of a strong base, preferably potassium-tert.butylate, sodium hydride or butyllithium, with an alkoxymethyl-phosphonium salt, preferably methoxymethyl-triphenyl-phosphonium chloride or methoxymethyl-triphenylphosphonium bromide. A cyclohexylcarbaldehyde according to formula IV is produced.

The cyclohexylcarbaldehyde IV is oxidized with a suitable oxidizing agent, preferably with potassium permanganate, chromium(VI)oxide or other chromium(VI)-salts, to form the corresponding cyclohexylcarboxylic acid. This carboxylic acid is reacted as such or as its corresponding hydrochloride with a dehydrating reagent, preferably with a carbodiimide, more preferably with dicyclohexyl-carbodiimide, in the presence of an activation reagent, preferably with 1-hydroxy benzotriazole, with an amine of formula $R^4R^5NH$ to form the corresponding amide according to formula V.

The protecting groups $S^1$ and $S^2$ are cleaved from the compound according to formula V, to form a 4-substituted cyclohexanone derivative according to formula VI.

The compound according to formula VI is reacted in the presence of a compound of formula $HNR^{O1}R^{O2}$ with a cyanide, preferably potassium cyanide or TMSCN, to form a 4-substituted 1-amino-1-cyano-cyclohexane derivative according to formula VII.

The aminonitrile according to formula VII is reacted with organometallic reagents, preferably Grignard or organolithium reagents, of the formula metal-$R^3$, to form the compounds according to the invention according to formula I.

The protecting groups at $R^{O1}$ and $R^{O2}$ are optionally subsequently cleaved by methods known to a person skilled in the art.

EXAMPLES

The following examples are intended to describe the invention in further detail without limiting the scope of the invention. The yields of compounds produced have not been optimized. All temperatures are uncorrected.

As used herein, the term "ether" denotes diethylether, "THF" tetrahydrofuran, "DMF" dimethylformamide, "EE" ethylacetate and "DCM" dichloromethane. The term "equivalent" denotes amount of substance equivalent, "mp" melting point or melting range, "decomp." decomposition, "RT" room temperature, "abs." absolute (anhydrous),"rac." racemic, "conc." concentrated, "min" minutes, "h" hours, "d" days, "vol. %" volume percent, "m %" mass percent and "M" is a concentration in mol/l.

Silica gel 60 (0.040-0.063 mm) from E. Merck, Darmstadt was used as the stationary phase for column chromatography. The thin-layer chromatography tests were carried out using HPTLC chromatoplates, silica gel 60 F 254, from E. Merck, Darmstadt. The mixing ratios of eluants for chromatographic tests are always given in volume/volume.

The compounds used in the following examples were either commercially available, or production thereof is known in the art or has been derived from the prior art in a manner obvious to persons skilled in the art.

4-dimethylamino-4-phenyl-cyclohexanecarbaldehyde 46 mmol (10.0 g) of 4-dimethylamino-4-phenylcyclohexanone were dissolved in toluene. This solution was added dropwise at 70° C. to a suspension of 138.1 mmol, (47.33 g) methoxymethyl triphenylphosphonium chloride and 138.1 mmol (25.82 g) potassium tert.-butylate. The mixture was stirred for a few more hours at 70° C., hydrolysed with water and extracted using EE. The combined organic phases were washed with saturated NaCl solution, dried over sodium sulphate and concentrated. The resultant brown resin was chromatographed using silica gel. The desired aldehyde is obtained as a cis/trans-mixture.

4-dimethylamino-4-phenyl-cyclohexanecarboxylic acid hydrochloride 4-dimethylamino-4-phenyl-cyclohexanecarbaldehyde (2,3 g, 10 mmol) was dissolved in THF (60 ml). Potassium permanganate (3 g, 19 mmol) was dissolved in 50 ml distilled water at 50° C., cooled to RT and added dropwise to the solution of the aldehyde, so the temperature was kept below 40° C. The mixture was stirred for 3 h at RT. Precipitated manganese dioxide was suction-filtered and washed thoroughly with THF and water in succession. The combined filtrates were evaporated and extracted with ether (3×15 ml). The pH was then adjusted to 1 using 2M hydrochloric acid and the mixture was shaken out again with ether (3×20 ml). The aqueous phase was evaporated to dryness. The residue was dried over $P_2O_5$. The solid was suspended in isopropanol (30 ml), the insoluble residue suction-filtered, the mother liquor evaporated and mixed with ether until cloudy. After cooling for 16 hours the resultant precipitate was suction-filtered, washed with ether and dried. 1.5 g (54%) of 4-dimethylamino-4-phenyl-cyclohexanecarboxylic acid hydrochloride with an mp of 112-130° C. were obtained by fractional precipitation.

2-[(4-dimethylamino-4-phenyl-cyclohexanecarbonyl) -amino]-3-(1H-indol-3-yl)-propionic acid-methylester-hydrochloride (Examples 1 and 2)

4-dimethylamino-4-phenyl-cyclohexanecarboxylic acid hydrochloride (568 mg, 2 mmol) and L-tryptophan-methylester-hydrochloride (509 mg, 2 mmol) were dissolved in 5 ml dry DMF and N-methylmorpholine (0.88 ml, 8 mmol) was added. After 10 minutes 1-hydroxybenzotriazole (1 g, 8 mmol) was added, the mixture cooled to 0° C. and dicyclohexylcarbodiimide (1.6 g, 8 mmol) introduced. For working up, the precipitate was suction-filtered and washed with cold DMF. The filtrate was added to a mixture of saturated NaCl-solution (93 ml) and saturated sodium hydrogen carbonate solution (7 ml). Ether was added, the phases were separated, the ether phase was dried and concentrated. A portion of the non-polar diastereoisomer (25 mg, 2.8%) was isolated from the residue (1.3 g) by chromatography. The aqueous phase was extracted with EE, adjusted to pH 10 with 1M NaOH and shaken out again with EE. The combined organic phases were dried and concentrated. The non-polar diastereoisomer (14 mg, 1.5%), the polar diastereoisomer (62 mg, 7%) and a mixed fraction (75 mg, 8.4%) were isolated from the residue (862 mg) by chromatography.

The non-polar diastereoisomer (72 mg, 0.16 mmol) was dissolved in ethanol (20 ml). 3.3 M ethanolic HCl (75 µl, 0.24 mmol) was added at RT and the mixture was stirred for 2 h. The solvent was distilled off and the residue ground with ether. The resultant solid was suction-filtered and washed with ether. The non-polar diastereoisomer of 2-[(4-dimethylamino-4-phenyl-cyclohexanecarbonyl)-amino]-3-(1H-indol-3-yl)-propionic acid methylester-hydrochloride was thus obtained as a beige solid (70.2 mg, 91%) with an mp of 138-144° C. (Example 1).

The process was carried out in a similar manner with the polar diastereoisomer (77 mg, 0.17 mmol). The hydrochloride of the polar diastereoisomer was thus obtained as a beige solid (83 mg, 99%) with an mp of 185-195° C. (Example 2).

4-dimethylamino-4-phenyl-cyclohexane carboxylic acid (3-phenyl-propyl)-amide hydrochloride (Examples 3 and 4)

4-dimethylamino-4-phenyl-cyclohexanecarboxylic acid hydrochloride (357 mg, 1.25 mmol) and 3-phenyl-propylamine-hydrochloride (170.1 mg, 1.25 mmol) were dissolved in dry DMF (6 ml) and N-methylmorpholine (0.28 ml, 2.5 mmol) was added. After 10 minutes 1-hydroxybenzotriazole (510 mg, 3.8 mmol) was added, the mixture cooled to 0° C., dicyclohexylcarbodiimide (778 mg, 3.8 mmol) introduced and stirred for 6 days at RT. For working up, the reaction mixture was cooled for 2 h, the solid suction-filtered and washed with cold DMF. A cooled mixture of saturated NaCl solution (46 ml) and saturated sodium hydrogen carbonate solution (4 ml) was added to the filtrate. Ether was added and the phases were separated. The ether phase was dried and concentrated. The aqueous phase was extracted with dichloromethane (4×10 ml). The dichloromethane extracts were dried and concentrated. The extraction residues were combined and purified by chromatography. The non-polar diastereoisomer (21 mg, 4%), a mixture (30 mg, 7%) and the polar diastereoisomer (109 mg, 24%) were obtained.

The non-polar diastereoisomer (20 mg, 0.05 mmol) was dissolved in ethanol (2 ml) and methylethylketone (2 ml). 3.3 M ethanolic HCl (25 µl, 0.08 mmol) was added at RT and stirred for 2 h. The solvent was distilled off and the residue ground with ether. The resultant solid was suction-filtered and washed with ether (2×1 ml). The non-polar diastereoisomer of 4-dimethylamino-4-phenyl-cyclohexanecarboxylic acid (3-phenyl-propyl)-amide hydrochloride was thus obtained as a light yellow solid (19 mg, 88%) with an mp of 100-105° C. (Example 3).

The process was carried out in a similar manner with the polar diastereomer (105 mg, 0.29 mmol). The hydrochloride of the polar diastereomer was thus obtained as a colorless solid (115 mg, 96%) with an mp of 112-115° C. (Example 4).

Tests of the Efficacy of the Compounds of the Invention

Measurement of ORL1 Binding

The cyclohexane derivatives of general formula I were investigated in a receptor binding assay using $^3$H-nociceptin/orphanin FQ with membranes of recombinant CHO-ORL1 cells. This test system was carried out by the method presented by Ardati et al. (Mol. Pharmacol. 51, 1997, pp. 816-824). The concentration of $^3$H-nociceptin/orphanin FQ was 0.5 nM in these tests. The binding assays were each carried out with 20 µg membrane protein per 200 µl batch 50 mM Hepes, pH 7.4, 10 mM $MgCl_2$ and 1 mM EDTA. The binding with the ORL1 receptor was determined using 1 mg WGA-SPA beads (Amersham-Pharmacia, Freiburg), by incubation of the batch for one hour at RT and subsequent measurement in the Trilux scintillation counter (Wallac, Finland). The affinity is shown in Table 1 as a nanomolar $K_i$ value in or % inhibition at c=1 µM.

Measurement of η-Binding

The receptor affinity for human µ-opiate receptor was determined in a homogeneous batch in microtitre plates. For this purpose, dilution series of the respective substituted cyclohexylcarboxylic acid derivatives to be tested were incubated with a receptor membrane preparation (15-40 µg protein per 250 µl incubation batch) of CHO-KL cells, which express the human L-opiate receptor (RB-HOM receptor membrane preparation from NEN, Zaventem, Belgium) in the presence of 1 nmol/l of the radioactive ligand [$^3$H]-naloxone (NET719, NEN, Zaventem, Belgium) and 1 mg WGA-SPA beads (wheat germ agglutinin SPA beads from Amersham/Pharmacia, Freiburg, Germany) in a total volume of 250 µl for 90 minutes at room temperature. 50 mmol/l tris-HCl supplemented with 0.05% by weight sodium azide and 0.06% by weight bovine serum albumin were added as an incubation buffer. 25 µmol/l naloxone were also added to determine the non-specific binding. At the end of the 90 minute incubation period, the microtitre plates were centrifuged off for 20 minutes at 1000 g and the radioactivity measured in a β-counter (Microbeta-Trilux, PerkinElmer Wallac, Freiburg, Germany). The percentage displacement of the radioactive ligand from its binding with the human μ-opiate receptor at a concentration of the test substances of 1 μmol/l was determined and given as a percentage inhibition (% inhibition) of the specific binding. $IC_{50}$ inhibition concentrations, which bring about a 50% displacement of the radioactive ligand, were partially calculated by taking as a basis the percentage displacement by various concentrations of the compounds of general formula I to be tested. $K_i$ values for the test substances were obtained by conversion by means of the Cheng-Prusoff equation.

Measurement of Serotonin Re-uptake

In order to carry out these in vitro studies, synaptosomes were freshly isolated from rat brain areas. What is known as a "$P_2$" fraction was used in each case. This was prepared in accordance with the instructions provided by Gray and Whittaker (E. G. Gray and V. P. Whittaker (1962) J. Anat. 76, 79-88). These vesicular particles were isolated from the medulla+pons region of male rats' brains for 5HT uptake. A detailed description of the method can be found in the literature (M.Ch. Frink, H.-H. Hennies, W. Englberger, M. Haurand and B. Wilfert (1996) Arzneim.-Forsch./Drug Res. 46 (III), 11, 1029-1036).

Measurement of Noradrenalin Re-uptake

In order to carry out these in vitro studies, synaptosomes were freshly isolated from areas of rats' brains. What is known as a "$P_2$" fraction was used in each case. This was prepared in accordance with Gray and Whittaker's directions (E. G. Gray and V. P. Whittaker (1962) J. Anat. 76, 79-88). These vesicular particles were isolated from the hypothalamus of male rats' brains for NA uptake. A detailed description of the method can be found in the literature (M.Ch. Frink, H.-H. Hennies, W. Englberger, M. Haurand and B. Wilfert (1996) Arzneim.-Forsch./Drug Res. 46 (III), 11, 1029-1036).

The following binding data was determined, by way of example:

| Example No. | ORL1% [1 μM] |
|---|---|
| 1 | 34.00 |
| 3 | 30.00 |

| Example No. | ORμnal % [1 μM] |
|---|---|
| 1 | 55 |
| 2 | 34 |
| 3 | 70.5 |
| 4 | 59 |

| Example No. | 5HT-uptake % inhibition [10 μM] |
|---|---|
| 1 | 74 |
| 2 | 56 |

-continued

| Example No. | 5HT-uptake % inhibition [10 μM] |
|---|---|
| 3 | 88 |
| 4 | 85 |

| Example No. | NA-uptake % inhibition [10 μM] |
|---|---|
| 1 | 30 |
| 3 | 65 |
| 4 | 71 |

Preparation of a Parenteral Solution of a Substituted Cyclohexylcarboxylic Acid Compound According to the Invention 3.8 g of the compound of Example 1 were dissolved at room temperature in 1 liter of water for injection purposes and then adjusted to isotonic conditions for injection purposes by adding anhydrous glucose.

This procedure for preparing a parenteral solution is fully applicable to the other substituted cyclohexylcarboxylic acid compounds according to the invention.

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted cyclohexylcarboxylic acid amide compound corresponding to formula I:

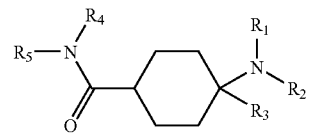

wherein $R^1$ and $R^2$ independently represent H; CHO; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; or respectively singly or multiply substituted or unsubstituted aryl, $C_{3-8}$ cycloalkyl or heteroaryl bound by $C_{1-3}$ alkyl; or $R^1$ and $R^2$ together represent $CH_2CH_2OCH_2CH_2$, $CH_2CH_2NR^{10}CH_2CH_2$ or $(CH_2)_{3-6}$, wherein $R^{10}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted aryl or heteroaryl; or respectively singly or multiply substituted or unsubstituted aryl, $C_{3-8}$ cycloalkyl or heteroaryl bound by $C_{1-3}$ alkyl;

$R^3$ represents respectively unsubstituted or singly or multiply substituted cyclopentyl, cyclohexyl, naphthyl, thiophenyl, benzothiophenyl, furyl, benzofuranyl, benzodioxolanyl, indolyl, indanyl, benzodioxanyl or pyridyl; respectively unsubstituted or singly or multiply substituted $C_{5-6}$ cycloalkyl, phenyl, naphthyl, anthracenyl, thiophenyl, benzothiophenyl, pyridyl, furyl, benzofuranyl, benzodioxolanyl, indolyl, indanyl, benzodioxanyl, pyrrolyl, pyrimidyl or pyrazinyl bound by a saturated, unbranched $C_{1-2}$ alkyl group; phenyl, 2-fluorophenyl, 3-fluorophenyl, 4-fluorophenyl, 2-chlorophenyl, 4-chlorophenyl, 3-chlorophenyl, 2-bromophenyl, 3-bromophenyl, 4-bromophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2-hydroxyphenyl, 3-hydroxyphenyl, 4-hydroxyphenyl, 2,3-dichlorophenyl, 3,4-dichlorophenyl, 3,5-dichlorophenyl, 2,4-dichlorophenyl, 2,3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert.-butylphenyl, 4-fluoro-3-chlorophenyl, 4-bromo-3-fluorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl, 5-fluoro-2-methoxyphenyl, 4-chloro-3-trifluoromethyl or 4-bromo-2-methylphenyl;

$R^4$ represents $-(CR^6R^7)_nR^8$, wherein n represents 0, 1, 2, 3, 4, 5 or 6, $R^6$ represents H or saturated or unsaturated, branched or unbranched, unsubstituted or singly or multiply substituted $C_{1-5}$ alkyl;

$R^7$ represents H, saturated or unsaturated, branched or unbranched, unsubstituted or singly or multiply substituted $C_{1-5}$ alkyl, or $COOR^9$, wherein $R^9$ represents H or saturated or unsaturated, branched or unbranched, unsubstituted or singly or multiply substituted $C_{1-5}$ alkyl; or $R^6$ and $R^7$ form a ring $(CH_2)_kCHR^8(CH_2)_m$, where k=1, 2 or 3 and m=1 or 2, and $R^8$ represents respectively unsubstituted or singly or multiply substituted $C_{3-8}$ cycloalkyl, aryl or heteroaryl; and $R^5$ represents H or $-(CH_2)_lR^8$, wherein l represents 1, 2 or 3, and $R^8$ has the meaning given above, or $R^4$ and $R^5$ together with represent $CH_2CH_2OCH_2CH_2$ or $CH_2CH_2NR^{11}CH_2CH_2$, wherein $R^{11}$ represents H; respectively saturated or unsaturated, branched or unbranched, singly or multiply substituted or unsubstituted $C_{1-5}$ alkyl; respectively saturated or unsaturated, singly or multiply substituted or unsubstituted $C_{3-8}$ cycloalkyl; respectively singly or multiply substituted or unsubstituted aryl or heteroaryl; or respectively singly or multiply substituted or unsubstituted aryl, $C_{3-8}$ cycloalkyl or heteroaryl bound by $C_{1-3}$ alkyl;

in the form of a pure stereoisomer or a mixture of isomers in any proportion, or a physiologically acceptable salt thereof.

2. A compound according to claim 1, wherein said compound in the form of a pure enantiomer or diastereomer.

3. A compound according to claim 1, wherein said compound is in the form of a racemic mixture.

4. A compound according to claim 1, wherein $R^1$ and $R^2$ independently represent H; saturated or unsaturated, branched or unbranched, singly or multiply substituted or unsubstituted $C_{1-5}$ alkyl, or $R^1$ and $R^2$ together form a ring and represent $CH_2CH_2OCH_2CH_2$, $CH_2CH_2NR^{10}CH_2CH_2$ or $(CH_2)_{3-6}$, wherein $R^{10}$ represents H; or saturated or unsaturated, branched or unbranched, singly or multiply substituted or unsubstituted $C_{1-5}$ alkyl.

5. A compound according to claim 4, wherein $R^1$ and $R^2$ independently represent $CH_3$ or H, with the proviso that $R^1$ and $R^2$ do not simultaneously represent H.

6. A compound according to claim 1, wherein $R^3$ represents respectively unsubstituted or singly or multiply substituted naphthyl, thiophenyl or pyridyl; respectively unsubstituted or singly or multiply substituted $C_{5-6}$ cycloalkyl, phenyl, naphthyl, thiophenyl, pyridyl bound by a saturated, unbranched $C_{1-2}$-alkyl group; phenyl, 2-fluorophenyl, 3-fluorophenyl, 4-fluorophenyl, 2-chlorophenyl, 4-chlorophenyl, 3-chlorophenyl, 2-cyanophenyl, 3-cyanophenyl, 4-cyanophenyl, 2-methylphenyl, 3-methylphenyl, 4-methylphenyl, 2-methoxyphenyl, 3-methoxyphenyl, 4-methoxyphenyl, 2-trifluoromethylphenyl, 3-trifluoromethylphenyl, 4-trifluoromethylphenyl, 2-ethylphenyl, 3-ethylphenyl, 4-ethylphenyl, 2-ethoxyphenyl, 3-ethoxyphenyl, 4-ethoxyphenyl, 2,3-dichlorophenyl, 3,4-dichlorophenyl, 3,5-dichlorophenyl, 2,4-dichlorophenyl, 2, 3-difluorophenyl, 3,4-difluorophenyl, 3,5-difluorophenyl, 2,4-difluorophenyl, 2-fluoro-3-chlorophenyl, 2-chloro-3-fluorophenyl, 2-chloro-4-fluorophenyl, 2-fluoro-4-chlorophenyl, 4-fluoro-3-chlorophenyl, 4-fluoro-3-methylphenyl, 4-tert.-butylphenyl, 4-fluoro-3-chlorophenyl, 3,5-bis(trifluoromethyl)phenyl, 4-chloro-2-trifluoromethylphenyl, 2-methoxy-5-methylphenyl, 5-chloro-2-methoxyphenyl, 4-phenoxyphenyl, 2-methylthiophenyl, 3-methylthiophenyl, 4-methylthiophenyl or 4-chloro-3-trifluoromethyl.

7. A compound according to claim 6, wherein $R^3$ represents pyridyl, phenyl, 3-fluorophenyl or 4-fluorophenyl.

8. A compound according to claim 7, wherein $R^3$ represents phenyl.

9. A compound according to claim 1, wherein $R^6$ represents H, and $R^7$ represents H or $COOR^9$.

10. A compound according to claim 1, wherein $R^5$ represents H.

11. A compound according to claim 1, wherein $R^8$ represents respectively unsubstituted or singly or multiply substituted cyclobutyl, cyclopropyl, cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl, fluorenyl, fluoranthenyl, benzothiazolyl, benzotriazolyl or benzyl[1,2,5]thiazolyl or 1.2-dihydroacenaphtenyl, pyridinyl, furanyl, benzofuranyl, pyrazolinonyl, oxopyrazolinonyl, dioxolanyl, adamantyl, pyrimidinyl, quinolinyl, isoquinolinyl, phthalazinyl or quinazolinyl.

12. A compound according to claim 11, wherein $R^8$ represents respectively unsubstituted or singly or multiply substituted cyclopentyl, cyclohexyl, cycloheptyl, cyclooctyl, anthracenyl, indolyl, naphthyl, benzofuranyl, benzothiophenyl, indanyl, benzodioxanyl, benzodioxolanyl, acenaphthyl, carbazolyl, phenyl, thiophenyl, furyl, pyridyl, pyrrolyl, pyrazinyl or pyrimidyl.

13. A compound according to claim 12, wherein $R^8$ represents respectively singly or multiply substituted phenyl or indolyl.

14. A compound according to claim 1, selected from the group consisting of:
- 2-[(4-dimethylamino-4-phenyl-cyclohexanecarbonyl) -amino]-3-(1H-indol-3-yl)-propionic acid-methylester-hydrochloride; non-polar diastereomer;
- 2-[(4-dimethylamino-4-phenyl-cyclohexanecarbonyl)-amino]-3-(1H-indol-3-yl)-propionic acid-methylester-hydrochloride; polar diastereomer;
- 4-dimethylamino-4-phenyl-cyclohexanecarboxylic acid carboxylic acid (3-phenyl-propyl)amide hydrochloride; non-polar diastereomer, and
- 4-dimethylamino-4-phenyl-cyclohexanecarboxylic acid (3-phenyl-propyl)-amide-hydrochloride; polar diastereomer, in the form of a pure stereoisomer or a mixture of isomers in any proportion, or a physiologically acceptable salt thereof.

15. A process for producing a substituted cyclohexylcarboxylic acid amide compound according to claim 1, said process comprising:
- reacting an alkoxymethyl-phosphonium salt in the presence of a strong base with a 4-aminocyclohexanone;
- subsequently oxidizing with an oxidizing agent, and
- reacting with an amine of formula $R^4R^5NH$ in the presence of a dehydrating reagent and an activation reagent.

16. A process according to claim 15, wherein said oxidizing agent is potassium permanganate, chromium(VI) oxide or a chromium(VI) salt; said dehydrating agent is a carbodiimide; said activation reagent is 1-hydroxybenzotriazole, and said organometallic reagent is a Grignard or organolithium reagent.

17. A process for producing a substituted cyclohexylcarboxylic acid amide compound according to claim 1, said process comprising:
- reacting a protected cyclohexane-1,4-dione in the presence of a strong base with an alkoxymethyl phosphonium salt;
- oxidizing with an oxidizing agent;
- reacting with an amine of formula $R^4R^5NH$ in the presence of a dehydrating reagent and an activation reagent;
- cleaving the protecting group;
- reacting with a cyanide in the presence of a compound of formula $HNR^{O1}R^{O2}$, and
- reacting with an organometallic reagent of the formula metal-$R^3$.

18. A pharmaceutical composition comprising a compound according to claim 1 and at least one pharmaceutical carrier or auxiliary.

19. A method or treating pain comprising administering to a patient an effective pain alleviating amount of a compound according to claim 1.

20. A method according to claim 19, wherein said pain is acute, visceral, neuropathic or chronic pain.

21. A method of treating anxiety, said method comprising administering to a patient in need thereof a pharmaceutically effective amount of a compound according to claim 1.

* * * * *